US012760325B2

(12) United States Patent
Chiang et al.

(10) Patent No.: US 12,760,325 B2
(45) Date of Patent: Oct. 13, 2026

(54) BIOACTIVE GLASS AS NUCLEIC ACID CARRIERS WITH pH SWITCH CONTROL-RELEASING

(71) Applicant: CORNING INCORPORATED, Corning, NY (US)

(72) Inventors: Pei-Chen Chiang, Tainan City (TW); Qiang Fu, Painted Post, NY (US); Cheng-I Hsu, Zhubei-si (TW); Wei-Lun Hsu, New Taipei City (TW)

(73) Assignee: CORNING INCORPORATED, Corning, NY (US)

( * ) Notice: Subject to any disclaimer, the term of this patent is extended or adjusted under 35 U.S.C. 154(b) by 1162 days.

(21) Appl. No.: 17/782,379

(22) PCT Filed: Dec. 9, 2020

(86) PCT No.: PCT/US2020/063861

§ 371 (c)(1),
(2) Date: Jun. 3, 2022

(87) PCT Pub. No.: WO2021/119043

PCT Pub. Date: Jun. 17, 2021

(65) Prior Publication Data

US 2023/0045516 A1 Feb. 9, 2023

Related U.S. Application Data

(60) Provisional application No. 62/945,779, filed on Dec. 9, 2019.

(51) Int. Cl.
*C12N 15/87* (2006.01)
*C03C 3/064* (2006.01)
(Continued)

(52) U.S. Cl.
CPC .............. *C12N 15/87* (2013.01); *C03C 3/064* (2013.01); *C03C 3/097* (2013.01); *C03C 3/112* (2013.01);
(Continued)

(58) Field of Classification Search
None
See application file for complete search history.

(56) References Cited

U.S. PATENT DOCUMENTS 5,945,525 A 8/1999 Uematsu et al.
6,290,991 B1 9/2001 Roser et al.
(Continued)

FOREIGN PATENT DOCUMENTS

CA 2146971 A1 4/1994
CN 104303054 A 1/2015
(Continued)

OTHER PUBLICATIONS

English translation of Zimmer et al. (WO 2004/076369). (Year: 2004).*
(Continued)

*Primary Examiner* — Ronak C Patel
(74) *Attorney, Agent, or Firm* — Travis B. Gasa; Svetlana Z. Short

(57) ABSTRACT

A pH-switchable carrier composition includes a plurality of bioactive glass particles, wherein each of the bioactive glass particle is optionally at least a partially coated with a surface modifier; wherein the bioactive glass particles, with or without, the surface modifier can bind to a nucleic acid compound upon contact at pH in the range of about 7 to about 11, and exhibit controlled release of the nucleic acid compound at pH in the range of about 5 to 6.

32 Claims, 7 Drawing Sheets

(51) Int. Cl.

| | |
|---|---|
| ***C03C 3/097*** | (2006.01) |
| ***C03C 3/112*** | (2006.01) |
| ***C03C 4/00*** | (2006.01) |
| ***C03C 8/06*** | (2006.01) |
| ***C03C 8/08*** | (2006.01) |
| ***C03C 8/16*** | (2006.01) |
| ***C03C 12/00*** | (2006.01) |
| ***C03C 17/28*** | (2006.01) |

(52) U.S. Cl.
CPC .......... *C03C 4/0014* (2013.01); *C03C 4/0035* (2013.01); *C03C 8/06* (2013.01); *C03C 8/08* (2013.01); *C03C 8/16* (2013.01); *C03C 12/00* (2013.01); *C03C 17/28* (2013.01); *C03C 2218/111* (2013.01); *C12N 2320/50* (2013.01)

(56) References Cited

U.S. PATENT DOCUMENTS

| | | | |
|---|---|---|---|
| 6,503,755 B1 | 1/2003 | Keating et al. | |
| 7,776,600 B2 | 8/2010 | Kumta et al. | |
| 8,137,697 B1 | 3/2012 | Sung et al. | |
| 9,463,245 B2 | 10/2016 | Avnir et al. | |
| 10,343,903 B2 | 7/2019 | Zink et al. | |
| 2002/0114768 A1 | 8/2002 | Stoor et al. | |
| 2006/0160085 A1 | 7/2006 | Hillebrand et al. | |
| 2009/0306359 A1 | 12/2009 | Hillebrand et al. | |
| 2011/0186524 A1* | 8/2011 | Sauer | H01F 1/0054 210/695 |
| 2014/0056954 A1 | 2/2014 | O'Donnell et al. | |
| 2015/0209757 A1 | 7/2015 | Onishi | |

FOREIGN PATENT DOCUMENTS

| | | | | |
|---|---|---|---|---|
| CN | 106186674 A | 12/2016 | | |
| CN | 107761252 A | 3/2018 | | |
| EP | 2770058 A1 | 8/2014 | | |
| WO | 2011/000865 A2 | 1/2011 | | |
| WO | 2015/007383 A1 | 1/2015 | | |
| WO | WO-2018025020 A1 * | 2/2018 | .......... | A61L 27/446 |
| WO | 2020/106514 A1 | 5/2020 | | |

OTHER PUBLICATIONS

English translation of Harttig et al. (DE 19854973) (Year: 2000).*

El-Fiqi Ahmed, et al, "Capacity of mesoporous bioactive glass nanoparticles to deliver therapeutic molecules", Nanoscale, vol. 4, No. 23, Jan. 2012 , pp. 7475.

International Search Report and Written Opinion of the International Searching Authority; PCT/US2020/063861; mailed on Jun. 24, 2021, 22 pages; European Patent Office.

Kamegawa Rimpei, et al, "Functionalization of silica nanoparticles for nucleic acid delivery", Nano Research, Tsinghua University Press, vol. 11, No. 10, Jun. 2018, pp. 5219-5239.

Tian Xia, et al, "Polyethyleneimine Coating Enhances the Cellular Uptake of Mesoporous Silica Nanoparticles and Allows Safe Delivery of siRNA and DNA Constructs", ACS Nano, vol. 3, No. 10, Oct. 2009, pp. 3273-3286.

Xiong Lin, et al, "Magnetic Core-Shell Silica Nanoparticles with Large Radial Mesopores for siRNA Delivery", Small, vol. 12, No. 34, May 2016, pp. 5-4742.

Auguste et al., "Triggered release of siRNA from poly(ethylene glycol)-protected, pH-dependent liposomes", Journal of Controlled Release, vol. 130, 2008, pp. 266-274.

Chinese Patent Application No. 202080085508.X, Office Action dated Nov. 28, 2023, 5 pages (English translation only), Chinese Patent Office.

Li et al., "Synthesis of radial mesoporous bioactive glass particles to deliver osteoactivin gene", J. Mater. Chem. B, 2014, vol. 2, pp. 7045-7054.

Petrakova et al., "Imaging of transfection and intracellular release of intact, non-labeled DNA using fluorescent nanodiamonds", Nanoscale, Nanoscale, 2016, vol. 8, pp. 12002-12012.

Romeisa et al., "Top-down processing of submicron 45S5 Bioglass® for enhanced in vitro bioactivity and biocompatibility", Procedia Engineering, vol. 102, 2015, pp. 534-541.

Zhang et al., "pH-Switchable Coordinative Micelles for Enhancing Cellular Transfection of Biocompatible Polycations", ACS Appl. Mater. Interfaces 2019, vol. 11, pp. 20689-20698.

* cited by examiner

| X2,000 | 876EKH | 890HFI | 890HFK |
|---|---|---|---|
| 65°C |  10μm 3.3μm-5.4μm |  10μm 3.5μm-6.2μm |  10μm 3.5μm-5.2μm |
| PEI |  10μm 4.1μm-6.3μm |  10μm 1.8μm-5.7μm |  10μm 1.7μm-3.8μm |
| Chitosan, shrimp shell |  10μm 3.3μm-7.2μm |  10μm 2.2μm-4.5μm |  10μm 2.7μm-4.2μm |
| Chitosan, Low MW |  10μm 4.3μm-7.6μm |  10μm 2.7μm-4.5μm |  10μm 2.1μm-3.9μm |

BIOACTIVE GLASS AS NUCLEIC ACID CARRIERS WITH pH SWITCH CONTROL-RELEASING

CROSS-REFERENCE TO RELATED APPLICATIONS

This application claims the benefit of priority under 35 U.S.C. § 371 of International Application No. PCT/US2020/063861, filed on Dec. 9, 2020, which claims the benefit of priority under 35 U.S.C. § 119 if U.S. Provisional Application No. 62/945,779, filed Dec. 9, 2019, the content of which is incorporated herein by reference in its entirety.

TECHNICAL FIELD

This disclosure relates to glass compositions for delivery of nucleic acids in to cells or microorganisms. In particular, the disclosure relates to bioactive glass compositions capable of capturing and control leasing the nucleic acids in the designated pH environment.

BACKGROUND

The application of utilizing or transferring the external nucleic acid for gene regulation or modulation is an emerging market, especially in the agriculture and therapeutics field. The ability of small interfering RNA (siRNA) to regulate gene expression has potential therapeutic applications, but its use is limited by inefficient delivery. The delivery of external nucleic acids into the target organs or cells remains specifically challenging due to the stability of nucleic acids and the cell uptake efficiency. Therefore, there is a strong need to explore new glass compositions having improved surface properties which could serve as nucleic acid carriers to enhance the cell uptake rate.

SUMMARY OF THE INVENTION

According to a first aspect, pH-switchable carrier composition comprises a plurality of bioactive glass particles, wherein each of the bioactive glass particle is optionally at least a partially coated with a surface modifier. In certain embodiments, the bioactive glass particles, with or without, the surface modifier can bind to a nucleic acid compound upon contact at pH in the range of about 7 to about 11, and exhibit controlled release of the nucleic acid compound at pH in the range of about 5 to about 6. In certain embodiments, the bioactive glass particle mainly comprises, expressed in terms of weight percent on the oxide basis, from about 30% to about 75% $SiO_2$, from about 2% to about 40% CaO and from about 3% to about 15% $P_2O_5$. In certain embodiments, the bioactive glass particle comprising about 75% $SiO_2$, from about 2% to about 40% CaO and from about 3% to about 15% $P_2O_5$ further comprises, expressed in terms of weight percent on the oxide basis: from about 0% to about 5% $B_2O_3$; from about 0% to about 5% $Al_2O_3$; from about 0% to about 20% MgO; from about 0% to about 10% $ZrO_2$; from about 0% to about 5% F; and from about 0% to about 30% $R_2O$, wherein $R_2O$ comprises from about 0% to about 10% $K_2O$ and from about 0% to about 30% $Na_2O$.

In other embodiments, the bioactive glass particle mainly comprises, expressed in terms of weight percent on the oxide basis, from about 30% to about 70% $B_2O_3$, from about 5% to about 25% CaO and from about 1% to about 10% $P_2O_5$. In certain embodiments, the bioactive glass particle comprising from about 30% to about 70% $B_2O_3$, from about 5% to about 25% CaO and from about 1% to about 10% $P_2O_5$ further comprises, expressed in terms of weight percent on the oxide basis: from about 0% to about 5% $SiO_2$; from about 0% to about 15% $Al_2O_3$; from about 0% to about 10% MgO; from about 0% to about 10% $ZrO_2$; from about 0% to about 5% F; and from about 0% to about 20% $R_2O$, wherein $R_2O$ comprises from about 0% to about 20% $K_2O$ and from about 0% to about 10% $Na_2O$.

In certain embodiments, the bioactive glass particle comprises a calcium phosphate glass. In certain embodiments, the bioactive glass particle is at least a partially coated with a surface modifier and the surface modifier comprises a polycationic compound. In certain embodiments, the polycationic compound is selected from the group consisting of polyamines, polylysine, polyarginine, polyornithine, polyalkylenimine, chitosan, poly alkyl aminoalkyl methacrylate and derivatives thereof, or any combination thereof. In certain embodiments, the polycationic compound is selected from the group consisting of polyethyleneimine, shrimp chitosan, low molecular weight chitosan and derivatives thereof. In certain embodiments, the molecular weight of low molecular weight chitosan or a derivative is from about 50 kDa to about 375 kDa.

In certain embodiments, wherein the nucleic acid compound is selected from the group consisting of ribonucleic acid compound, deoxyribonucleic acid compound, or derivatives thereof. In certain embodiments, the bioactive glass particles have a particle size of about 1 μm to about 10 μm. In certain embodiments, the bioactive glass particles have a particle size of about 1 μm to about 5 μm. In certain embodiments, the zeta-potential of the unmodified bioactive glass particles is from about −10 mV to about −40 mV under neutral conditions. In certain embodiments, the zeta-potential of the surface modified bioactive glass particles is from about 0 mV to about −20 mV under neutral conditions. In certain embodiments, the concentration of the nucleic acid ranges from about 5 ng/mg to about 10 μg/mg of the total weight of the carrier composition.

According to a second aspect, a bioactive glass particle is optionally at least a partially coated with a surface modifier; wherein the bioactive glass particle, with or without, the surface modifier can bind to a nucleic acid compound upon contact at pH in the range of about 7 to about 11, and exhibit controlled release of the nucleic acid compound at pH in the range of about 5 to about 6; and wherein the bioactive glass particle mainly comprises, expressed in terms of weight percent on the oxide basis: (a) from about 30% to about 75% $SiO_2$, from about 2% to about 40% CaO and from about 3% to about 15% $P_2O_5$; or (b) from about 30% to about 70% $B_2O_3$, from about 5% to about 25% CaO and from about 1% to about 10% $P_2O_5$.

According to a third aspect, a method of manufacturing a bioactive glass carrier comprises processing a bioactive glass into fine particles; mixing the fine particles of bioactive glass with a liquid medium to form a solution; optionally modifying the surface of the bioactive glass particles in the solution with a surface modifier, contacting the bioactive glass particles with a nucleic acid compound in a liquid medium to form an admixture; incubating the admixture under conditions in which the nucleic acid compound non-covalently binds to the bioactive glass particles. In certain embodiments, the method comprising modifying the surface of the bioactive glass particles by incubating the bioactive glass particles with a surface modifier. In certain embodiments, the surface modifier comprises a polycationic compound. In certain embodiments, the incubation of bioactive glass particles with a surface modifier is conducted at a temperature of about ambient temperature to about 65° C. In certain embodiments, the incubation of bioactive glass particles with a surface modifier is conducted for a period of about 8 to 24 h.

In certain embodiments of the third aspect, the method further comprises contacting the surface-modified bioactive glass particles with a nucleic acid compound in a liquid medium to form an admixture; and incubating the admixture under conditions in which the nucleic acid compound non-covalently binds to the surface-modified bioactive glass particles. In certain embodiments, incubation of the surface-modified bioactive glass particles with the nucleic acid is conducted at room temperature. In certain embodiments, incubation of the surface-modified bioactive glass particles with the nucleic acid is conducted for a period of about 15 min to 2 h. In certain embodiments of the method, the liquid medium is selected from the group consisting of water, alcohols or hydrocarbons.

In certain embodiments of the method of the third aspect, the bioactive glass particle mainly comprises, expressed in terms of weight percent on the oxide basis, from about 30% to about 75% $SiO_2$, from about 2% to about 40% CaO and from about 3% to about 15% $P_2O_5$. In certain embodiments, the bioactive glass particle comprising about 75% $SiO_2$, from about 2% to about 40% CaO and from about 3% to about 15% $P_2O_5$ further comprises, expressed in terms of weight percent on the oxide basis: from about 0% to about 5% $B_2O_3$; from about 0% to about 5% $Al_2O_3$; from about 0% to about 20% MgO; from about 0% to about 10% $ZrO_2$; from about 0% to about 5% F; and from about 0% to about 30% $R_2O$, wherein $R_2O$ comprises from about 0% to about 10% $K_2O$ and from about 0% to about 30% $Na_2O$.

In certain embodiments of the method of the third aspect, the bioactive glass particle mainly comprises, expressed in terms of weight percent on the oxide basis, from about 30% to about 70% $B_2O_3$, from about 5% to about 25% CaO and from about 1% to about 10% $P_2O_5$. In certain embodiments, the bioactive glass particle comprising from about 30% to about 70% $B_2O_3$, from about 5% to about 25% CaO and from about 1% to about 10% $P_2O_5$ further comprises, expressed in terms of weight percent on the oxide basis: from about 0% to about 5% $SiO_2$; from about 0% to about 15% $Al_2O_3$; from about 0% to about 10% MgO; from about 0% to about 10% $ZrO_2$; from about 0% to about 5% F; and from about 0% to about 20% $R_2O$, wherein $R_2O$ comprises from about 0% to about 20% $K_2O$ and from about 0% to about 10% $Na_2O$.

According to a fourth aspect, a vehicle comprises the pH-switchable carrier composition according to the first aspect. In certain embodiments, the composition comprises a plurality of bioactive glass particles, wherein each of the bioactive glass particle is optionally at least a partially coated with a surface modifier. In certain embodiments, the bioactive glass particles, with or without, the surface modifier can bind to a nucleic acid compound upon contact at pH in the range of about 7 to about 11, and exhibit controlled release of the nucleic acid compound at pH in the range of about 5 to about 6. In certain embodiments, the vehicle comprises a drug delivery vehicle, a gene delivery vehicle, a tissue regeneration vehicle, a crop treatment or crop protection, an immunomodulatory vehicle, or a gene editing complex vehicle.

DETAILED DESCRIPTION

Figure 1:
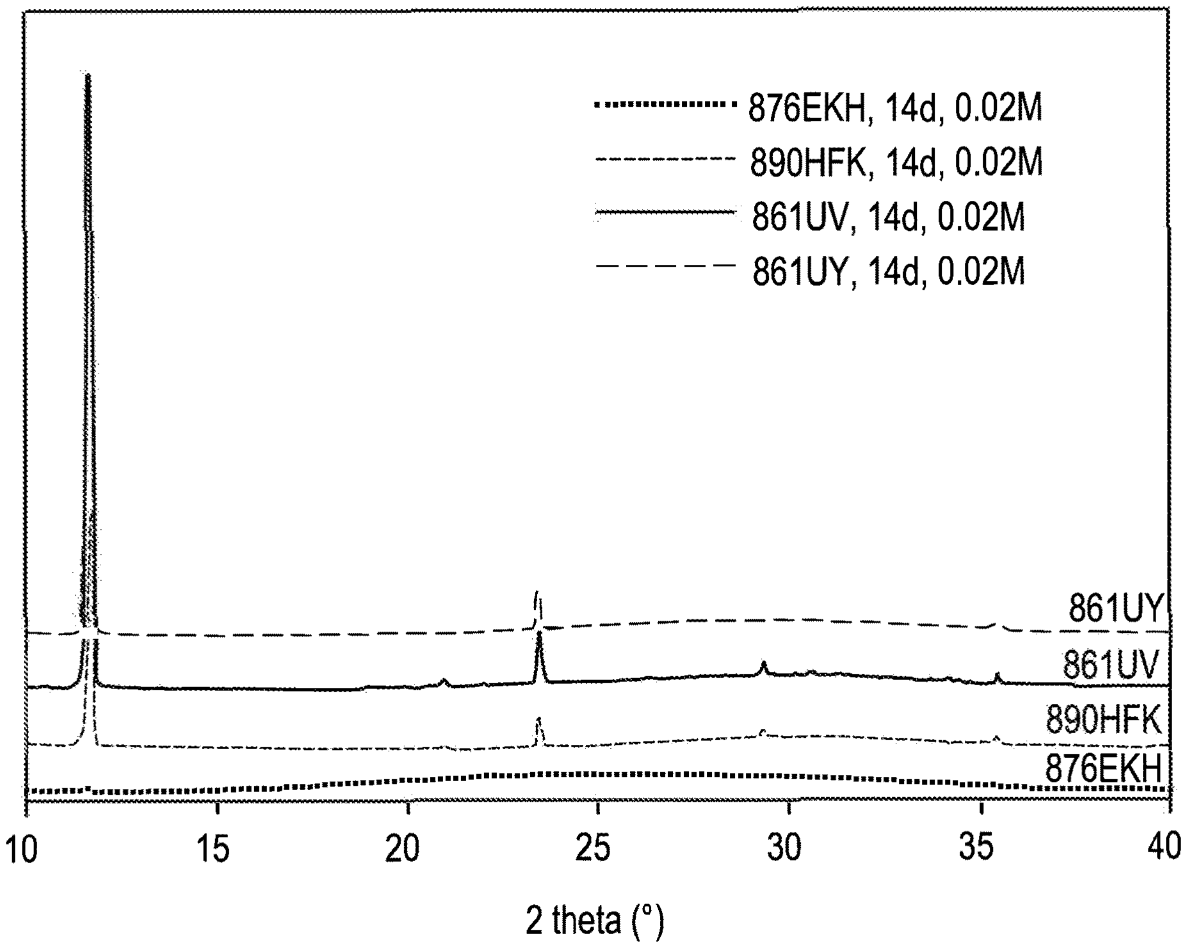
FIG. 1 shows X-ray diffraction (XRD) pattern for the bioactive glass particles in accordance with one or more embodiments shown and described herein.

Reference will now be made in detail to various embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments.

As discussed above, the present technology generally relates to glass compositions and methods for the delivery of a desired material, such as nucleic acid, into cells and tissues. In various embodiments, provided herein are compositions and systems including bioactive glass particles useful for the delivery of therapeutic agents to cells or tissues of plants, animals and insects, and methods for making and using the same.

The definitions of certain terms as used in this specification are provided below. Unless defined otherwise, all technical and scientific terms used herein generally have the same meaning as commonly understood by one of ordinary skill in the art to which the present technology belongs.

As used in this specification and the appended claims, the singular forms "a", "an" and "the" include plural referents unless the content clearly dictates otherwise. Thus, for example, reference to "a" component includes aspects having two or more such components, unless the context clearly indicates otherwise. For example, reference to "a cell" includes a combination of two or more cells, and the like. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Generally, the nomenclature used herein and the laboratory procedures in cell culture, molecular genetics, organic chemistry, analytical chemistry and nucleic acid chemistry described below are those well-known and commonly employed in the art.

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising. Other elements may optionally be present other than the elements specifically identified by the "and/or" clause, whether related or unrelated to those elements specifically identified. As a non-limiting example, a reference to "X and/or Y" can refer, in one embodiment, to X only (optionally including elements other than Y); in some embodiments, to Y only (optionally including elements other than X); in yet some embodiments, to both X and Y (optionally including other elements).

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the term "particle size" refers to particle diameter unless otherwise stated. The particle size is expressed for example as peak particle size which represents the hydrodynamic diameter of the particles by dynamic light scattering (DLS) techniques, or mean particle size or average particle size.

As used herein the terms "bioactive glass" (BAG) or "biologically active glass" mean an inorganic glass material having an oxide of silicon or an oxide of boron as its major component and which is capable of binding with desired biological material, such as nucleic acid, cells and tissues.

As used herein, the term "tunable" or "switchable" refers to a bioactive glass carrier that changes its behavior in response to environmental stimuli. As an example, pH switchable carriers can demonstrate switchable behavior based on pH, where the carrier is capable of binding to nucleic acids at a particular pH and eluting the nucleic acids at another pH.

As used herein, the term "controlled release" refers to release of the nucleic acid from a nanoparticles according to a predetermined profile. In some aspects, the selected controlled release may include the release of the nucleic acid compound in a particular pH range.

Compositions

Various aspects and/or embodiments of this disclosure relate to compositions including bioactive glass. In various embodiments, provided herein is a pH-switchable carrier compositions which includes bioactive glass particles, wherein the carrier can demonstrate switchable behavior based on pH. The carrier is capable of binding to nucleic acids at a particular pH and eluting the nucleic acids at another pH. The compositions disclosed herein exhibit excellent biocompatibility. The bioactive nature of the glass results from a series of complex physiochemical reactions on the surface of the glass under physiological conditions. For example, when the glass is exposed to a body fluid inside an animal or insect, cation exchange may occur, such that the cations from the glass surface are replaced by protons from solution. The interfacial pH becomes more alkaline and is accompanied by the release of the $Ca^{2+}$ and $PO_4^{3-}$ ions into solution due to the network dissolution taking place on the glass surface This favors the formation of brushite ($CaHPO_4 \cdot 2H_2O$), a known bioactive ceramic, or hydroxyapatite (HCA), which are capable of binding to interfacial metabolites, collagen and glycoproteins. Bioactive glasses have therefore found medical applications, e.g., in the field of orthopedics and dentistry. The present technology aims to provide a bioactive glass with enhanced bioactivity.

In one aspect, provided herein are pH-switchable carrier compositions which include bioactive glass particles, wherein the bioactive glass particle is optionally at least a partially coated with a surface modifier and wherein the bioactive glass particles, with or without, the surface modifier can bind to a nucleic acid compound upon contact at pH in the range of about 7 to about 11, and exhibit controlled release of the nucleic acid compound at pH in the range of about 5 to about 6.

The bioactive glass of the carrier compositions may be formed from precursor glass compositions from silicate and borate families that exhibit excellent nucleic acid capturing/releasing efficiency in the different pH environment. Suitable glass precursor materials for use in the technology include, without limitation, oxides of silicon, boron, phosphorus, potassium, sodium, calcium, lithium, aluminum, magnesium, zirconium, rubidium, cesium, strontium, barium, chromium, titanium, tungsten, iron, and zinc. The glass may additional contain a halide, such as fluoride. The biocompatibility and degradation of the composition are influenced by the composition of the bioactive glass. In various embodiments, the bioactive glass particle may include a calcium phosphate glass.

In various embodiments, the precursor glass composition for the bioactive glass includes $SiO_2$. When the content of $SiO_2$ is too small, the glass may have poor chemical and mechanical durability. On the other hand, when the content of $SiO_2$ is too large, melting ability of the glass decreases since the melting temperature of pure $SiO_2$ is too high. With increasing $SiO_2$ content, the bioactivity of glass decreases. In certain embodiments, the precursor glass composition for the bioactive glass may include a silicate glass, which includes $SiO_2$ as the primary glass-forming oxide. In various embodiments for the silicate glass, $SiO_2$ is present in the precursor glass composition in an amount from about 30 wt. % to about 75 wt. %, such as from about 35 wt. % to about 70 wt. %, from about 40 wt. % to about 65 wt. %, from about 45 wt. % to about 60 wt. %, from about 50 wt. % to about 55 wt. %, of the total weight of the precursor glass composition, or any range including and/or in-between any two of these values.

In certain embodiments, the silicate glass compositions include from about 0 wt. % $B_2O_3$ to about 5 wt. % $B_2O_3$, such as from about 0.2 wt. % to about 4.5 wt. %, from about 0.5 wt. % to about 4 wt. %, from about 1 wt. % to about 3.5 wt. %, from about 1.5 wt. % to about 3 wt. %, or from about 2 wt. % to about 2.5 wt. % $B_2O_3$, of the total weight of the precursor glass composition, or any range including and/or in-between any two of these values.

In certain embodiments, the precursor glass composition for the bioactive glass may include a borate glass, which includes $B_2O_3$ as the primary glass-forming oxide. Borate glass is much less durable than silicate glass, making it attractive for fast degradation. In various embodiments for the borate glass, $B_2O_3$ is present in the precursor glass composition in an amount from about 30 wt. % to about 70 wt. %, such as from about 35 wt. % to about 65 wt. %, from about 40 wt. % to about 60 wt. %, from about 45 wt. % to about 55 wt. %, from about 50 wt. % to about 55 wt. %, of the total weight of the precursor glass composition, or any range including and/or in-between any two of these values.

In certain embodiments, the borate glass compositions include from about 0 wt. % $SiO_2$ to about 5 wt. % $SiO_2$, such as from about 0.2 wt. % to about 4.5 wt. %, from about 0.5 wt. % to about 4 wt. %, from about 1 wt. % to about 3.5 wt. %, from about 1.5 wt. % to about 3 wt. %, or from about 2 wt. % to about 2.5 wt. % $SiO_2$, of the total weight of the precursor glass composition or any range including and/or in-between any two of these values.

In another aspect, a bioactive glass particle is provided, which is optionally at least a partially coated with a surface modifier; wherein the bioactive glass particle, with or without, the surface modifier can bind to a nucleic acid compound upon contact at pH in the range of about 7 to about 11, and exhibit controlled release of the nucleic acid compound at pH in the range of about 5 to about 6; and wherein the bioactive glass particle mainly comprises, expressed in terms of weight percent on the oxide basis: (a) from about 30% to about 75% $SiO_2$, from about 2% to about 40% CaO and from about 3% to about 15% $P_2O_5$; or (b) from about 30% to about 70% $B_2O_3$, from about 5% to about 25% CaO and from about 1% to about 10% $P_2O_5$.

In another aspect, a bioactive glass particle is provided, which is optionally at least a partially coated with a surface modifier; wherein the bioactive glass particle, with or without, the surface modifier can bind to a nucleic acid compound upon contact at pH in the range of about 7 to about 11, and exhibit controlled release of the nucleic acid compound at pH in the range of about 5 to about 6; and wherein the bioactive glass particle mainly comprises, expressed in terms of weight percent on the oxide basis: (a) from about 30% to about 75% $SiO_2$, from about 2% to about 40% CaO and from about 3% to about 15% $P_2O_5$; or (b) from about 30% to about 70% $B_2O_3$, from about 5% to about 25% CaO and from about 1% to about 10% $P_2O_5$.

The precursor glass composition for the bioactive glass may also include $P_2O_5$ which serves as a network former. Furthermore, the liberation of phosphate ions to the surface of bioactive glasses contributes to the formation of Ca—P compounds such as brushite or apatite. The provision of phosphate ions by the bioactive glass increases mineral formation rate and the binding capacity of the bone tissue. In addition, $P_2O_5$ increases the viscosity of the glass, which in turn expands the range of operating temperatures, and is therefore an advantage to manufacture and formation of the glass. In various embodiments, $P_2O_5$ is present in the precursor glass composition in an amount from about 0 wt. % to about 20 wt. %, of the total weight of the precursor glass composition, including from about 1 wt. % to about 10 wt. % and about 3 wt. % to about 15 wt. % of $P_2O_5$, based on the total weight of the precursor glass composition. In certain embodiments, the silicate glass compositions include from about 3 wt. % $P_2O_5$ to about 15 wt. % $P_2O_5$, such as from about 4 wt. % to about 14 wt. %, from about 5 wt. % to about 13 wt. %, from about 6 wt. % to about 12 wt. %, from about 7 wt. % to about 11 wt. %, or from about 8 wt. % to about 10 wt. %, of the total weight of the precursor glass composition, or any range including and/or in-between any two of these values. In certain embodiments, the borate glass compositions include from about 1 wt. % to about 10 wt. %, such as from about 2 wt. % to about 9 wt. %, from about 3 wt. % to about 8 wt. %, from about 4 wt. % to about 7 wt. %, or from about 5 wt. % to about 6 wt. % $P_2O_5$, of the total weight of the precursor glass composition, or any range including and/or in-between any two of these values.

The precursor glass composition for the bioactive glass may also include $Al_2O_3$ and $ZrO_2$ which help in improving the chemical durability in the borate glass while having no toxicity concerns. In various embodiments, $Al_2O_3$ is present in the precursor glass composition for the bioactive glass in an amount from about 0 wt. % to about 20 wt. %, of the total weight of the precursor glass composition, including from about 0 wt. % to about 5 wt. % and about 0.1 wt. % to about 15 wt. % of $Al_2O_3$, based on the total weight of the precursor glass composition. In certain embodiments, the silicate glass compositions include 0 wt. % $Al_2O_3$ to about 5 wt. % $Al_2O_3$, such as from about 0.2 wt. % to about 4.5 wt. %, from about 0.5 wt. % to about 4 wt. %, from about 1 wt. % to about 3.5 wt. %, from about 1.5 wt. % to about 3 wt. %, or from about 2 wt. % to about 2.5 wt. % $Al_2O_3$, of the total weight of the precursor glass composition, or any range including and/or in-between any two of these values. In certain embodiments, the borate glass compositions include from about 0.1 wt. % $Al_2O_3$ to about 15 wt. % $Al_2O_3$, such as from about 0.5 wt. % to about 12 wt. %, from about 1 wt. % to about 10 wt. %, from about 3 wt. % to about 8 wt. %, or from about 5 wt. % to about 7 wt. % $Al_2O_3$, of the total weight of the precursor glass composition, or any range including and/or in-between any two of these values.

In various embodiments, $ZrO_2$ is present in the precursor glass compositions, both silicate and borate, in an amount from about 0 wt. % $ZrO_2$ to about 10 wt. % $ZrO_2$, of the total weight of the precursor glass composition, such as from about 2 wt. % to about 9 wt. % from about 3 wt. % to about 8 wt. %, from about 4 wt. % to about 7 wt. %, or from about 5 wt. % to about 6 wt. % $ZrO_2$, of the total weight of the precursor glass composition, or any range including and/or in-between any two of these values.

The precursor glass composition for the bioactive glass may also include alkali oxides ($Li_2O$, $Na_2O$, $K_2O$, $Rb_2O$, and $Cs_2O$) which serve as aids in achieving low melting temperature and low liquidus temperatures, and improve bioactivity. In various embodiments, $Na_2O$ is present in the precursor glass composition for the bioactive glass in an amount from about 0 wt. % to about 35 wt. %, of the total weight of the precursor glass composition, including from about 0 wt. % to about 30 wt. % $Na_2O$ and about 0 wt. % to about 10 wt. % of $Na_2O$, based on the total weight of the precursor glass composition. In certain embodiments, the silicate glass compositions include 0 wt. % $Na_2O$ to about 30 wt. % $Na_2O$, such as from about 2 wt. % to about 25 wt. %, from about 5 wt. % to about 20 wt. %, from about 7 wt. % to about 15 wt. %, from about 8 wt. % to about 12 wt. %, or from about 9 wt. % to about 10 wt. % $Na_2O$, of the total weight of the precursor glass composition, or any range including and/or in-between any two of these values. In certain embodiments, the borate glass compositions include from about 0 wt. % $Na_2O$ to about 10 wt. % $Na_2O$, such as from about 0.5 wt. % to about 9 wt. %, from about 1 wt. % to about 8 wt. %, from about 2 wt. % to about 7 wt. %, or from about 5 wt. % to about 6 wt. % $Na_2O$, of the total weight of the precursor glass composition, or any range including and/or in-between any two of these values.

In various embodiments, $K_2O$ is present in the precursor glass composition for the bioactive glass in an amount from about 0 wt. % to about 25 wt. %, of the total weight of the precursor glass composition, including from about 0 wt. % to about 10 wt. % $K_2O$ and about 0 wt. % to about 20 wt. % of $K_2O$, based on the total weight of the precursor glass composition. In certain embodiments, the silicate glass compositions include from about 0 wt. % $K_2O$ to about 10 wt. % $K_2O$, such as from about 0.5 wt. % to about 9 wt. %, from about 1 wt. % to about 8 wt. %, from about 2 wt. % to about 7 wt. %, or from about 5 wt. % to about 6 wt. % $K_2O$, of the total weight of the precursor glass composition, or any range including and/or in-between any two of these values. In certain embodiments, the borate glass compositions include 0 wt. % $K_2O$ to about 20 wt. % $K_2O$, such as from about 2 wt. % to about 18 wt. %, from about 5 wt. % to about 15 wt. %, from about 6 wt. % to about 12 wt. %, or from about 8 wt. % to about 10 wt. % $K_2O$, of the total weight of the precursor glass composition, or any range including and/or in-between any two of these values.

In various embodiments, the precursor glass composition for the bioactive glass may include divalent cation oxides (such as alkaline earth oxides) which improve the melting behavior and the bioactivity of the glass. CaO is found to be able to react with $P_2O_5$ to form apatite when immersed in a simulated body fluid (SBF) or in vivo. The release of $Ca^{2+}$ ions from the surface of the glass contributes to the formation of a layer rich in calcium phosphate. In various embodiments, CaO is present in the precursor glass composition for the bioactive glass in an amount from about 0 wt. % to about 50 wt. %, of the total weight of the precursor glass composition, including from about 2 wt. % to about 40 wt. % and about 5 wt. % to about 25 wt. % of CaO, based on the total weight of the precursor glass composition. In certain embodiments, the silicate glass compositions include from about 2 wt. % CaO to about 40 wt. % CaO, such as from about 5 wt. % to about 35 wt. %, from about 10 wt. % to about 30 wt. %, from about 15 wt. % to about 25 wt. %, or from about 18 wt. % to about 22 wt. % CaO, of the total weight of the precursor glass composition, or any range including and/or in-between any two of these values. In certain embodiments, the borate glass compositions include 5 wt. % CaO to about 25 wt. % CaO, such as from about 7 wt. % to about 22 wt. %, from about 10 wt. % to about 20 wt. %, from about 12 wt. % to about 18 wt. %, or from about 15 wt. % to about 18 wt. % CaO, of the total weight of the precursor glass composition, or any range including and/or in-between any two of these values.

In various embodiments, MgO is present in the precursor glass composition in an amount from about 0 wt. % to about 25 wt. %, of the total weight of the precursor glass composition, including from about 0 wt. % to about 20 wt. % and about 0 wt. % to about 10 wt. % of MgO, based on the total weight of the precursor glass composition. In certain embodiments, the silicate glass compositions include from about 0 wt. % MgO to about 10 wt. % MgO, such as from about 0.5 wt. % to about 9 wt. %, from about 1 wt. % to about 8 wt. %, from about 2 wt. % to about 7 wt. %, from about 3 wt. % to about 6 wt. %, or from about 4 wt. % to about 5 wt. % MgO, of the total weight of the precursor glass composition, or any range including and/or in-between any two of these values. In certain embodiments, the borate glass compositions include 0 wt. % MgO to about 20 wt. % MgO, such as from about 0.5 wt. % to about 18 wt. %, from about 1 wt. % to about 15 wt. %, from about 3 wt. % to about 10 wt. %, or from about 5 wt. % to about 8 wt. % MgO, of the total weight of the precursor glass composition, or any range including and/or in-between any two of these values.

The glass compositions may also optionally include a small amount of fluoride. In certain embodiments, the precursor glass compositions, both silicate and borate, include from about 0 wt. % F to about 5 wt. % F, such as from about 0.2 wt. % F to about 4.5 wt. % F, from about 0.5 wt. % F to about 4 wt. % F, from about 1 wt. % F to about 3.5 wt. % F, from about 1.5 wt. % F to about 3 wt. % F, or from about 2 wt. % F to about 2.5 wt. % F, of the total weight of the precursor glass composition, or any range including and/or in-between any two of these values.

In various embodiments, the bioactive glass particle mainly includes, expressed in terms of weight percent on the oxide basis, from about 30% to about 75% $SiO_2$, from about 2% to about 40% CaO and from about 3% to about 15% $P_2O_5$. In such embodiments, the bioactive glass particle further includes, expressed in terms of weight percent on the oxide basis, from about 0% to about 5% $B_2O_3$; from about 0% to about 5% $Al_2O_3$; from about 0% to about 20% MgO; from about 0% to about 10% $ZrO_2$; from about 0% to about 5% F; and from about 0% to about 30% $R_2O$, wherein $R_2O$ comprises from about 0% to about 10% $K_2O$ and from about 0% to about 30% $Na_2O$.

In various embodiments, the bioactive glass particle mainly includes, expressed in terms of weight percent on the oxide basis, from about 30% to about 70% $B_2O_3$, from about 5% to about 25% CaO and from about 1% to about 10% $P_2O_5$. In such embodiments, the bioactive glass particle further includes, expressed in terms of weight percent on the oxide basis, from about 0% to about 5% $SiO_2$; from about 0% to about 15% $Al_2O_3$; from about 0% to about 10% MgO; from about 0% to about 10% $ZrO_2$; from about 0% to about 5% F; and from about 0% to about 20% $R_2O$, wherein $R_2O$ comprises from about 0% to about 20% $K_2O$ and from about 0% to about 10% $Na_2O$.

Exemplary silicate glass compositions may include, as represented in weight percentage, 30 to 75% $SiO_2$,
3 to 15% $P_2O_5$,
0 to 5% $B_2O_3$,
0 to 5% $Al_2O_3$,
0 to 30% $Na_2O$,
0 to 10% $K_2O$,
0-20% MgO,
2-40% CaO,
0-10% $ZrO_2$,
0-5% F.

Exemplary borate glass compositions may include, as represented in weight percentage, 0 to 5% $SiO_2$,
30 to 70% $B_2O_3$,
1 to 10% $P_2O_5$,
0.1 to 15% $Al_2O_3$,
0 to 10% $Na_2O$,
0 to 20% $K_2O$,
0-10% MgO,
5-25% CaO,
0-10% $ZrO_2$,
0-5% F.

In certain embodiments, the bioactive glass may be ground into fine particles in the range of 1-10 μm by air jet milling. The particle size can be varied in the range of 1-100 μm using attrition milling or ball milling of glass frits. Furthermore, these glasses can be subsequently processed into submicron using different methods, such as planetary ball milling or wet milling. The complex composition is possible but not easily achieved by bottom-up process, such as sol-gel formation. Another effective method to produce bioactive glass particle formation with precise size control is utilizing microreactors, such as Corning Advanced Flow Reactors. On an industrial scale, the glass particles of desired size may be produced using the top-down melting approach followed by milling or grinding, which affords flexibility of composition design and low cost of manufacturing. In certain embodiments, the bioactive glass may be ground into fine particles using air jet, ball milling or grinding. The glass particles of desired size can be used as such or may be incorporated into a polymer matrix depending the targeted applications.

The bioactive glass particles may bind to a nucleic acid compound under various pH conditions. The nucleic acid may coat or be located on the surface of the bioactive glass particle. Suitable nucleic acids include any ribonucleic acid (RNA) or deoxyribonucleic acid (DNA), which may be unmodified or modified. In various embodiments, nucleic acid includes, without limitation, single- and double-stranded RNA, single- and double-stranded DNA, RNA that is mixture of single- and double-stranded regions, DNA that is a mixture of single- and double-stranded regions, and hybrid molecules comprising DNA and RNA that may be single-stranded or, more typically, double-stranded or a mixture of single- and double-stranded regions. In addition, nucleic acid refers to triple-stranded regions comprising RNA or DNA or both, DNAs or RNAs containing one or more modified bases, and DNAs or RNAs with backbones modified for stability or for other reasons. In some embodiments, the nucleic acid includes ribonucleic acid, deoxyribonucleic acid, or derivatives thereof. In some embodiments, the nucleic acid includes ribonucleic acid or derivatives thereof. In other embodiments, the nucleic acid includes deoxyribonucleic acid or derivatives thereof. In some embodiments, the nucleic acid includes interfering ribonucleic acid molecules.

In various embodiments, the bioactive glass particle is at least a partially coated with a surface modifier. In various embodiments, the surface modifier may include compounds or compositions which facilitate the delivery of nucleic acid to the cells. For example, the surface modifier may include cationic compounds, which are compounds having polar groups that are positively charged at or around physiological pH. Exemplary cationic compounds include, without limitation, polycations, cationic lipids, cationic polymers or mixtures thereof. In various embodiments, the surface modifier includes a polycationic compound. The polycation to be used as surface modifier may be a synthetic polymer, a naturally occurring polymer or a chemically modified naturally occurring polymer. The polycation suitably has a plurality of positively charged groups at pH between 5 and 11. The charged groups may be selected among alkyl amines (including primary, secondary, tertiary and quaternary amines), imine, guanidium and aromatic amines. Suitable polycations include, without limitation, polyamines, polylysine, polyarginine, polyornithine, polyalkylenimine, chitosan, oligopeptides, cationized polysaccharides, cationized vegetal proteins or cationized animal proteins, protamines, activated dendrimers, diethylaminoethyl-dextran, polyamidoamines, poly(beta-aminoesters), aminopolysaccharides polypropylenimine, polyallylamine, polyvinylamine homo- or copolymer, poly(vinylpyridin), homo- or copolymer, poly (meth) acrylate homo- or copolymer, poly(meth)acrylamide homo- or copolymer, and derivatives thereof, cationic compounds that include peptides and protein fragments or combinations thereof. Examples of preferred n is polyethyleneimine (PEI), Hexadimethrine bromide (available under the trade name polybrene), polyhexamethylene guanidine (PHMG), polyhexamethylene biguanidine, polyallylamine, guanidinylated poly(allyl amine), polyaminopropylmethacrylamide, poly-[N-(3-guanidinopropyl)methacrylamide], poly aminoethyl (meth)acrylate, polydimethylaminoethylmethacrylate (PDMAEMA). In various embodiments, the polycationic compound is selected from the group consisting of polyamines, polylysine, polyarginine, polyornithine, polyalkylenimine, chitosan, poly alkyl aminoalkyl methacrylate and derivatives thereof, or any combination thereof. The chitosan may include, low molecular weight chitosan, high molecular weight chitosan or chitosan obtained from crustacean shells such as shrimp. In various embodiments, the polycation includes polyethyleneimine (PEI). In various embodiments, the polycation includes low molecular weight chitosan. In various embodiments, the polycation includes shrimp chitosan. In various embodiments, the polycationic compound is selected from the group consisting of polyethyleneimine, shrimp chitosan, low molecular weight chitosan and derivatives thereof.

The polycation may be branched or linear. For example, in the case of PEI, linear polyethyleneimines contain all secondary amines, in contrast to branched PEIs which contain primary, secondary and tertiary amino groups. It is hypothesized that these compounds facilitate delivery of nucleic acids into the cells because of their ability to neutralize the electrical charge of nucleic acids. The net cationic charge is maintained under alkaline conditions for certain applications. As a consequence, the nucleic acid remains bound to the polycation which provides some protection against degradation by nucleases (the polycation/nucleic acid complex is known to exhibit a better stability than the uncomplexed form). The polycation may contain one or several type of amino groups having different pKa values. The polycation may be a homopolymer or a copolymer. When the positively charged polymer is a copolymer the comonomer to be copolymerized with the monomer comprising the charge amino group is selected in order to maintain a sufficient level of water solubility to the copolymer. Other water soluble polycations may be selected among chitosan and its derivatives such as trimethyl chitosan, guanidilated chitosan, cationized polysaccharides such as DEAE Dextran and cationized vegetal proteins or cationized animal proteins.

In various embodiments, the molecular weight of low molecular weight chitosan or a derivative is from about 50 kDa to about 375 kDa, including without limitation, from about 75 kDa to about 350 kDa, from about 100 kDa to about 300 kDa, from about 150 kDa to about 250 kDa, or from about 180 kDa to about 220 kDa, or any range including and/or in-between any two of these values.

The critical properties to substantiate the capability and capacity of nucleic acid loading on the carriers are surface charge and surface area. The surface charge can be directly determined by zeta potential measurement. The more the positive charge on the carrier surface, the higher the potency to capture the negative charge of nucleic acid. On the other hand, the nucleic acid capture and releasing must be controllable and reversible. The carried nucleic acid should be released while delivered into the target. It is known that the pH value inside the cells is slightly acidic compared to the body fluids. Hence, the negative surface charge of carriers in acidic solution is required for nucleic acid releasing. The binding of nucleic acid on the surface or the surface modifier on the surface of the bioactive glass particles may be studied using the change in zeta-potential of the bioactive glass particle surface. A change in zeta-potential is indicative of the ligand binding to the surface of the bioactive glass particle or to the surface modifier. The zeta-potential is a measure of surface charge on the bioactive glass particles and may have an impact on the stability of particles under various pH conditions. In various embodiments, the zeta-potential of the unmodified bioactive glass particles is from about −10 mV to about −40 mV under neutral conditions, including, from about −10 mV to about 0 mV, −5 mV to about 0 mV, from about 0 mV to about 10 mV, 0 mV to about 20 mV, from about 0 mV to about 30 mV, from about 0 mV to about 40 mV, from about −10 mV to about 10 mV, −10 mV to about 20 mV, from about −10 mV to about 30 mV, or any range including and/or in-between any two of these values. In various embodiments, the zeta-potential of the surface modified bioactive glass particles is from about 0 mV to about −20 mV under neutral conditions, including, from about 0 mV to about −5 mV, 0 mV to about −10 mV, from about 0 mV to about −15 mV, from about 0 mV to about −18 mV, or any range including and/or in-between any two of these values.

The surface area of the bioactive glass particles can be varied by changing the particle size. The bioactive glass particles of the composition have narrow particle size distributions and optimum hydrodynamic diameter. A narrower range of particle sizes corresponds to a more uniform distribution of particle sizes. The bioactive glass particles have a 5 particle size of less than about 100 μm, such as for example less than about 90 μm, less than about 80 μm, less than about 70 μm, less than about 60 μm, less than about 50 μm, less than about 40 μm, less than about 30 μm, less than about 20 μm, less than about 10 μm, or less than about 5 μm. The 5 particle size of the bioactive glass particles can range from about 1 μm to about 100 μm, such as from about 5 μm to about 90 μm, from about 10 μm to about 80 μm, from about 20 μm to about 70 μm, from about 30 μm to about 60 μm, or from about 40 μm to about 50 μm, or any range including and/or in-between any two of these values. In various embodiments, the bioactive glass particles have a 5 particle size range of from about 1 μm to about 10 μm. In various embodiments, the bioactive glass particles have a particle size range of from about 1 μm to about 5 μm.

The bioactive glass particles, with or without the surface modification, exhibit enhanced capacity for nucleic acid loading onto the surface of the particles. Consequently, the nucleic acid loading is much higher and compatible with several applications. In various embodiments, the concentration of nucleic acid loaded on to the bioactive glass particle ranges from about 5 ng/mg to about 10 μg/mg of the total weight of the carrier composition, including from about 10 ng/mg to about 5 μg/mg, from about 100 ng/mg to about 1 μg/mg, from about 1 μg/mg to about 10 μg/mg, from about 2 μg/mg to about 9 μg/mg, from about 3 μg/mg to about 8 μg/mg, from about 4 μg/mg to about 7 μg/mg, or from about 5 μg/mg to about 6 μg/mg, from about 10 ng/mg to about 1 μg/mg, from about 20 ng/mg to about 500 ng/mg, from about 30 ng/mg to about 100 ng/mg, from about 40 ng/mg to about 80 ng/mg, from about 50 ng/mg to about 60 ng/mg, or any range including and/or in-between any two of these values. In certain embodiments, the concentration of the nucleic acid ranges from about 5 ng/mg to about 10 μg/mg of the total weight of the carrier composition. In certain embodiments, the concentration of the nucleic acid ranges from about 100 ng/mg to about 10 μg/mg of the total weight of the carrier composition. In certain embodiments, the concentration of the nucleic acid ranges from about 5 ng/mg to about 100 ng/mg of the total weight of the carrier composition.

In various embodiments, the capability of nucleic acid capturing and releasing is demonstrated with artificial DNA surrogate as ~200 bp which mimic the typical RNAi fragment length. The payload of glass composition without modifier would be probably sufficient for many applications, but the surface modifier can enhance the capacity of nucleic acid loading effectively (FIG. 6, DNA payload) under neutral conditions. The captured DNA can be quantitatively released in the slightly acidic buffer system with significantly lower eluting time, e.g., 30 minutes or less eluting time. This demonstrates the potential of the composition with or without modifier for nucleic acid transfer and delivery into the target.

A further advantage of the carrier compositions is that the glass particles are eventually degraded in nature even in the absence of uptake by the cells. The degradation rate of the carrier particles can be traced by Ca ion concentration in solution (FIG. 7, Ca trace), which demonstrates that the glass particles quickly release Ca ion in the first 24 hours, and then slowly but steadily degraded with the time. The particles can be ultimately completely degraded in nature and all the components are non-toxic to the environment.

Although the embodiments described herein are with respect to nucleic acid, the bioactive glass particles may be used as a carrier for other suitable therapeutic agents or medicaments which may include any compound or substance which is used to treat or prevent any given disease or disorder or in the regulation of a physiological condition in a human or animal subject. In some embodiments, the therapeutic agent may include an antibiotic, an antifungal, a peptide, a protein, a polymer, or combinations thereof. In some embodiments, the bioactive glass particles may include other therapeutic agents in addition to the nucleic acid. Suitable nucleic acids and therapeutic agents may be selected from the group consisting of genes, shRNAs, siRNAs, microRNAs, DNA fragments, RNA fragments, plasmids, and combinations thereof.

Methods

A variety of methods may be used to produce the bioactive glass particles and carrier compositions described herein. For example, the bioactive glass may first be produced by methods which include melting a batch of precursor glasses at a suitable temperature, in a suitable melting apparatus for a sufficient period of time to melt the batch of precursor glasses, annealing the glass at a suitable temperature; casting the molten glasses; and cooling the glass to room temperature. Suitable pre-cursor glasses are disclosed herein.

Depending on the composition, the precursor glasses can be melted at a temperature in the range of about 1000 to about 1600° C., preferably at a temperature in the range of about 1100 to about 1500° C., more preferably at a temperature in the range of about 1150° C. to about 1450° C., in a suitable apparatus, e.g., a covered platinum crucible, for a time sufficient to melt the glasses, such as e.g., about 60 min to about 24 h, including from about 90 min to about 20 h, about 2 h to about 18 h, about 5 h to about 16 h, or about 8 h to about 12 h, or any range including and/or in-between any two of these values. After melting and fining, the glasses can be poured and annealed at a temperature of about 350° C. to about 550° C., such as about 400° C. to about 500° C. The annealed glasses can then be cast in to a suitable mold, following which the resulting materials were left to cool at furnace rate. The glass materials thus formed are sized in to suitable particle size using methods known in the art such as milling and grinding.

Aspects of the present technology relate to a method for manufacturing a bioactive glass carrier. In various embodiments, the method includes processing a bioactive glass into fine particles; mixing the fine particles of bioactive glass with a liquid medium to form a solution; optionally modifying the surface of the bioactive glass particles in the solution with a surface modifier, contacting the bioactive glass particles with a nucleic acid compound in a liquid medium to form an admixture; and incubating the admixture under conditions in which the nucleic acid compound non-covalently binds to the bioactive glass particles.

In various embodiments, the modification of the surface of the bioactive glass particles may be done by incubating the bioactive glass particles with a surface modifier. For example, the surface modification on the glass particles can be conducted by mixing an aqueous solution of the surface modifier, e.g., polycationic polymers, such as chitosan or polyethyleneimine, with the glass particles. The blended mixture can then be incubated at an elevated temperature with gentle shaking for a period of time to form coating layers. Finally, the coated, surface modified bioactive glass particles are properly rinsed to remove the excess polymers and to ensure no interference from polymer aggregated particles. In various embodiments, incubation of the bioactive glass particles with a surface modifier is conducted at a temperature of about ambient temperature to about 65° C., including without limitation, from about 20° C. to 65° C., from about 30° C. to 65° C., from about 35° C. to 65° C., from about 40° C. to 65° C., or from about 50° C. to 65° C., or any range including and/or in-between any two of these values. In various embodiments, incubation of the bioactive glass particles with a surface modifier is conducted for a period of about 8 to 24 h, including, without limitation, from about 9 h to about 22 h, from about 10 h to about 20 h, from about 12 h to about 18 h, or from about 15 h to about 16 h or any range including and/or in-between any two of these values.

In various embodiments, the method further includes contacting the surface-modified bioactive glass particles with a nucleic acid compound in a liquid medium to form an admixture, and incubating the admixture under conditions in which the nucleic acid compound non-covalently binds to the surface-modified bioactive glass particles. In various embodiments, the incubation of surface-modified bioactive glass particles with the nucleic acid is conducted at room temperature. In various embodiments, the incubation of surface-modified bioactive glass particles with the nucleic acid is conducted for a period of about 15 min to 2 h, including, without limitation, from about 20 min to about 100 min, from about 30 min to about 80 min, from about 40 min to about 60 min, or from about 45 min to about 55 min, or any range including and/or in-between any two of these values. In various embodiments, the coating of nucleic acid on to the surface of the bioactive glass particles can be conducted in a suitable liquid medium such as water, alcohols or hydrocarbons.

Another aspect of the present technology relates to a vehicle comprising the pH-switchable carrier compositions described herein. The vehicle may include a drug delivery vehicle, a gene delivery vehicle, a tissue regeneration vehicle, a crop treatment or crop protection, an immunomodulatory vehicle, or a gene editing complex vehicle. The vehicle can be used to deliver the bioactive glass particles and carrier compositions described herein to various types of cells. Any type of cell which is susceptible to delivery of nucleic acids may be used as the target for transformation according to the present technology. Examples include, without limitation insect cells, animal cells and embryos, fungi, fish, yeast, and plant cells. The stable aqueous suspension may be used as part of phytosanitary compositions for controlling pest. For example, the stable suspensions may be used to protect crop against insects, in which case the nucleic acid is insecticidal double stranded RNA. The compositions and suspensions may be used in the prevention and/or control of pest infestation of plants, using interfering ribonucleic acid (RNA) molecules. Compositions and combinations containing the interfering RNA molecules of the technology for use in topical applications, for example in the form of insecticides.

For delivery to animal cells, the carrier compositions can be delivered by intravenous, intramuscular, or intraperitoneal injection to provide systemic (and possibly local when administered intramuscularly or intraperitoneally) anti-inflammatory effects. These effects can be therapeutic and/or prophylactic. In one embodiment, the particles are administered locally, for example, by inhalation, by spraying (in the form of an aerosol) or by mixing the particles with a gel (for example, a biocompatible hydrogel), cream or other aqueous or non-aqueous carrier, and applying or injecting the composition subcutaneously at a site at which surgery is to be performed at a later time. The compositions can advantageously include other carriers and additives. For delivery to plant cells, the carrier compositions may be administered using various methods known in the art, such as by spraying, drip-feeding, or irrigation. Aspects of the present technology relate to a method of protecting a crop against an insect, the method comprising administering the carrier compositions including the bioactive glass particles described herein to the crop. In various embodiments, the method includes protecting a crop against hemiptera, coleoptera, siphonaptera, dichyoptera, lepidoptera, orthoptera and diptera. In such methods, the nucleic acid in the composition may include insecticidal double stranded ribonucleic acid. Another aspect of the present technology relates to methods for down-regulating expression of a target gene in an insect pest species in order to prevent and/or control pest infestation, comprising contacting said pest species with an effective amount the carrier compositions described herein comprising at least one interfering ribonucleic acid (RNA). Suitable interfering RNA's are known in the art.

It will be apparent to those skilled in the art that various modifications and variations may be made without departing from the spirit or scope of the claimed subject matter. Accordingly, the claimed subject matter is not to be restricted except in light of the attached claims and their equivalents.

EXAMPLES

Various embodiments will be further clarified by the following examples, which are in no way intended to limit this disclosure thereto.

Example 1: Preparation of Bioactive Glass Composition

Exemplary bioactive glasses described herein are silicate or borate glasses which include a base composition comprising, in weight percent on the oxide basis, of the constituents listed in Table 1.

TABLE 1

| Oxides (wt. %) | BAG # 4 (890HFI) | BAG # 5 (861UV) | BAG # 6 (861UY) | BAG # 7 (890HFK) | BAG # 8 (876EKH) |
|---|---|---|---|---|---|
| $SiO_2$ | 0.4 | 42.8 | 41.2 | 0.4 | 62.1 |
| $B_2O_3$ | 50.3 | 0 | 0 | 52.5 | 0 |
| $P_2O_5$ | 3.2 | 9.5 | 9.1 | 3.3 | 7.0 |
| $Al_2O_3$ | 10.8 | 0 | 0 | 0.1 | 0 |
| $Na_2O$ | 4.9 | 0 | 0 | 5.1 | 21.3 |
| $K_2O$ | 9.8 | 0 | 0 | 10.3 | 5.3 |
| MgO | 4.1 | 14.4 | 13.9 | 4.3 | 0 |
| CaO | 16.4 | 32.4 | 31.1 | 17.1 | 4.3 |
| $ZrO_2$ | 0 | 0 | 3.9 | 6.8 | 0 |
| $F^-$ | 0 | 0.8 | 0.8 | 0 | 0 |
| Annealing point (° C.) | 500 | 400 | 400 | 500 | 460 |

Figure 2:
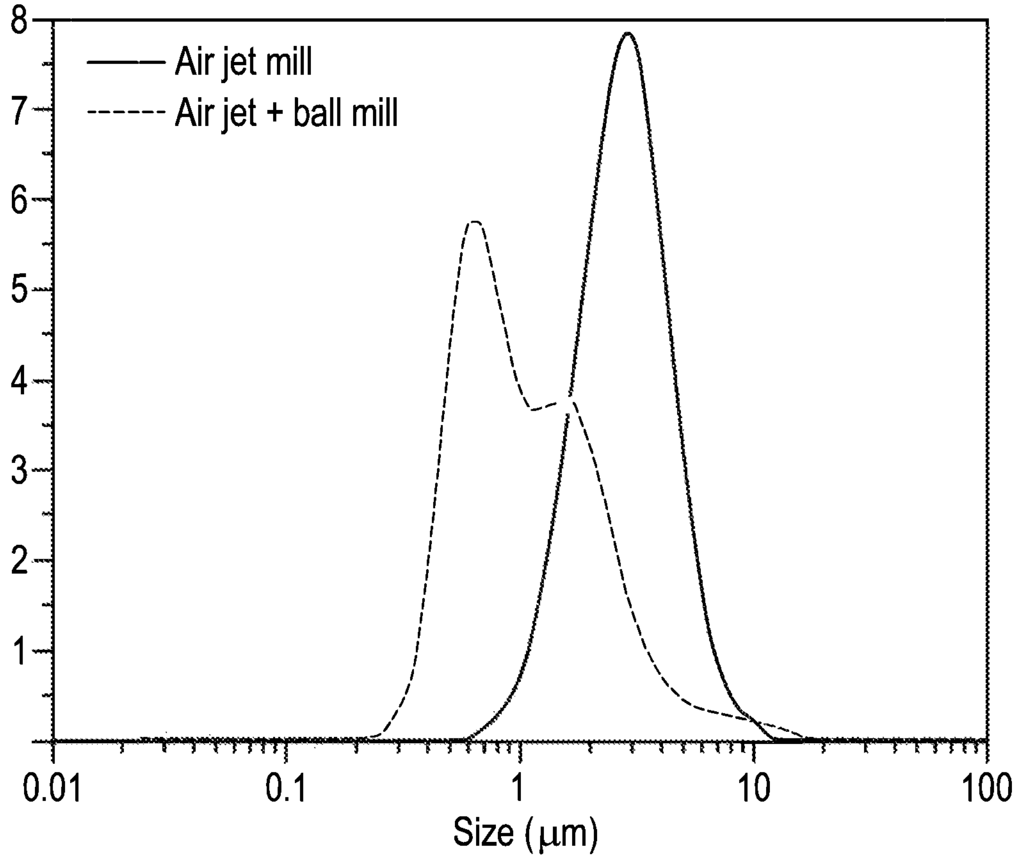
FIG. 2 is a graph showing the particle size distribution of an exemplary bioactive glass composition in accordance with one or more embodiments shown and described herein.

The glasses were made in a platinum crucible using a batch of raw materials listed in Table 1. Each crucible containing a formulated raw materials batch was placed in a preheated furnace and were melted at 1100-1500° C. for 16 h. The glasses were refined to produce molten precursor glass that was then cast into 7×11 inch blocks precursor glass that were annealed for annealed at temperatures ranging from 400-500° C. as noted in the table. The glasses were crushed using air jet and ball mill. FIG. 2 shows the particle size distribution of BAG #8 (876EKH) after air jet and ball mill processing. An additional ball mill can reduce D50 form 2.6 μm (after air jet mill) to 0.9 μm.

Identity of the crystalline phases of crystal phase assemblages and/or crystal sizes of a crystalline phase were determined by X-ray diffraction (XRD) analysis techniques known to those in the art, using such commercially available equipment as the Bruker D4 Endeavor diffractometer manufactured by Bruker Corporation, Massachusetts, United States. Spectra were typically acquired for 2θ from 10 to 40 degrees. XRD analysis was performed on the glasses and the results obtained are as shown in Table 2. FIG. 1 shows XRD pattern for glass powder after immersing in 0.02 M $KH_2PO_4$ solution for 14 days. The formation of brushite ($CaHPO_4 \cdot 2H_2O$) indicates the excellent biocompatibility of these glass compositions. Higher crystallinity was observed in UV and UY (BAG #5 and BAG #6) samples than in HFK or EKH (BAG #7 and BAG #8), suggesting a better bioactivity of the former.

TABLE 2

| Atomic % | BAG only | PEI | Chitosan, shrimp shell | Chitosan, Low MW |
|---|---|---|---|---|
| Si | 19.55 | 11.51 | 10.86 | 6.02 |
| P | 3.04 | 1.94 | — | — |
| Na | 0.48 | — | — | 0.25 |
| K | 0.71 | — | 0.29 | — |
| Ca | 6.41 | 4.20 | 1.07 | 0.67 |
| O | 69.80 | 45.69 | 48.43 | 35.62 |
| C | — | 36.66 | 39.35 | 57.45 |

Example 2: Surface Modification of Bioactive Glass Composition and Characterization In a 1.5 mL microtube was added 100 mg bioactive glass (BAG) prepared according to the process of Example 1, and 1 mL water and the mixture was vortex mixed while aliquot. Three sets of PEI (polyethyleneimine, AL-408727-100ML, branched, ~MW 25,000) solution were prepared. 100 mg of each PEI solution was transferred to a 1.5 mL microtube to which 0.8 mL water was add. The resulting solution was warmed in a 65° C. dry bath for 10 minutes. Similarly, three sets of low MW chitosan (AL-448869-50G, low MW, pre-treated with alkali deacetylation) solution were prepared. 10 mg of each chitosan powder was transferred to a 1.5 mL microtube to which 0.8 mL 0.3% acetic acid (30 μL HOAc/10 mL water) was added. The solution was vortexed for 1 min. Finally, three sets of shrimp shell chitosan (AL-417963-25G, from shrimp shells, pre-treated with alkali deacetylation) solution were prepared 10 mg of each chitosan granules was transferred to a 1.5 mL microtube to which 0.8 mL 0.3% acetic acid (30 μL HOAc/10 mL water) was added. The solution was vortexed for 1 min.

200 μL of BAG well suspension solution was combined with 800 μL of water, the prepared PEI and the prepared low MW and shrimp chitosan solutions, and incubated at 65° C. on dry bath for 20 hours. The mixtures are purified by ultracentrifugation at 15000 rpm for 5 min. The supernatant was disregarded, and the residue was washed with 400 μL water and centrifuge at 15000 rpm for 5 min. The purification steps were repeated twice.

The surface modified BAG particle solutions were resuspended in 800 μL water. Two sets of sets aliquot, one for analysis and one for DNA binding evaluation were collected. The set for analysis was maintained without solution at room temperature until analysis.

Figure 3:
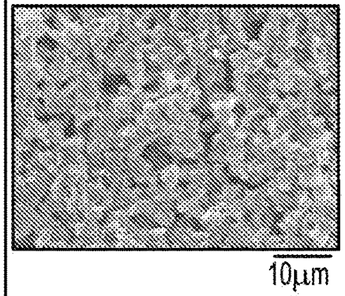
FIG. 3 illustrates SEM images of carrier compositions and surface modified bioactive glass particles in accordance with one or more embodiments shown and described herein.
Figure 3:
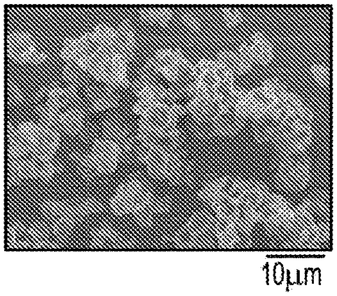
Figure 3:
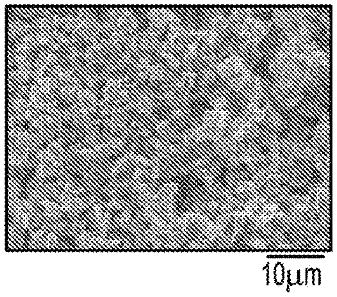
Figure 3:
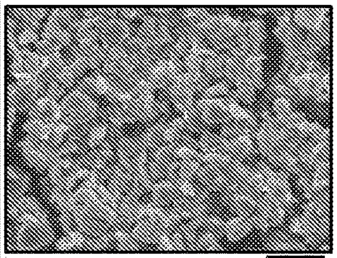
Figure 3:
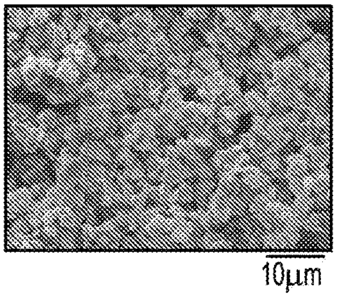
Figure 3:
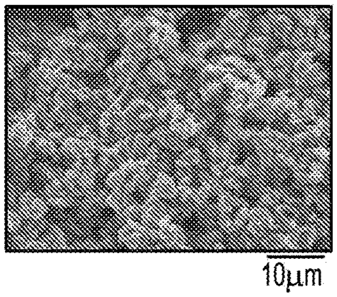
Figure 3:
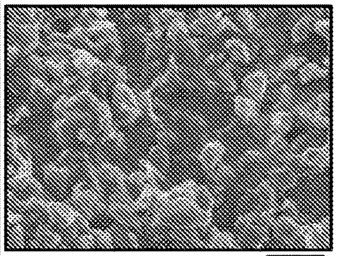
Figure 3:
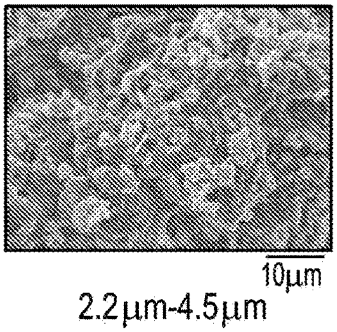
Figure 3:
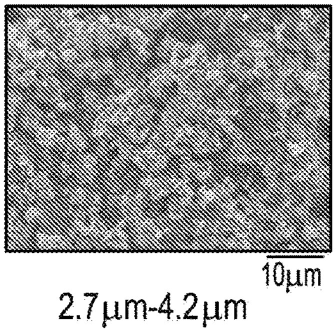
Figure 3:
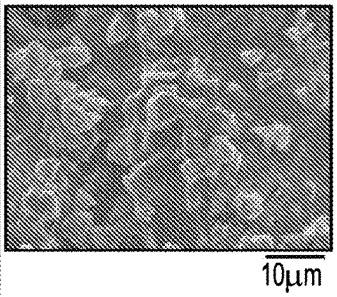
Figure 3:
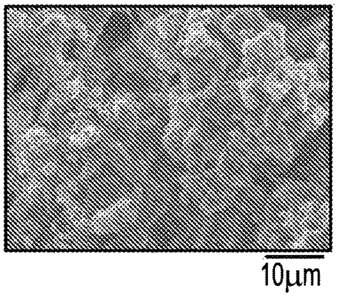
Figure 3:
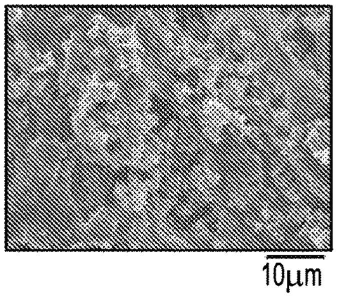
Figure 4:
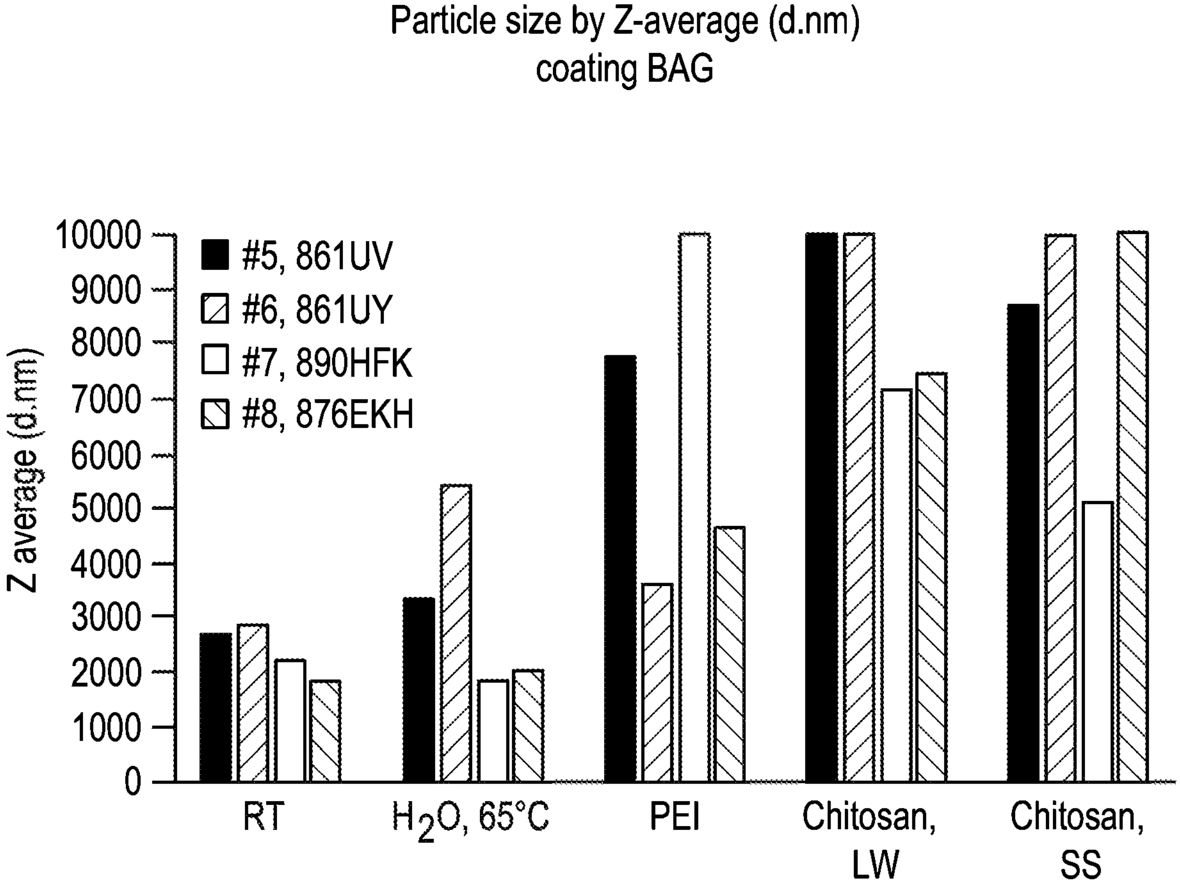
FIG. 4 is a bar graph showing the particle size distribution of the bioactive glass particles by DLS in accordance with one or more embodiments shown and described herein.

The chemical composition of the bioactive glass with/without modifiers, the brief particle size and morphology, were examined by scanning electron microscopy (SEM, JEOL JSM-6500F with EDS detector). The SEM images are shown in FIG. 3. The particle size measurement was also examined by Dynamic Light Scattering (Malvern Zetasizer Nano ZS) based on Brownian motion and estimated by Z-average size (FIG. 4). It is observed that the size of surface modified glass particles are slightly larger than the original particles, and the modifier on the glass particle surface are confirmed by SEM-EDX semi-quantitative analysis.

Figure 5A:
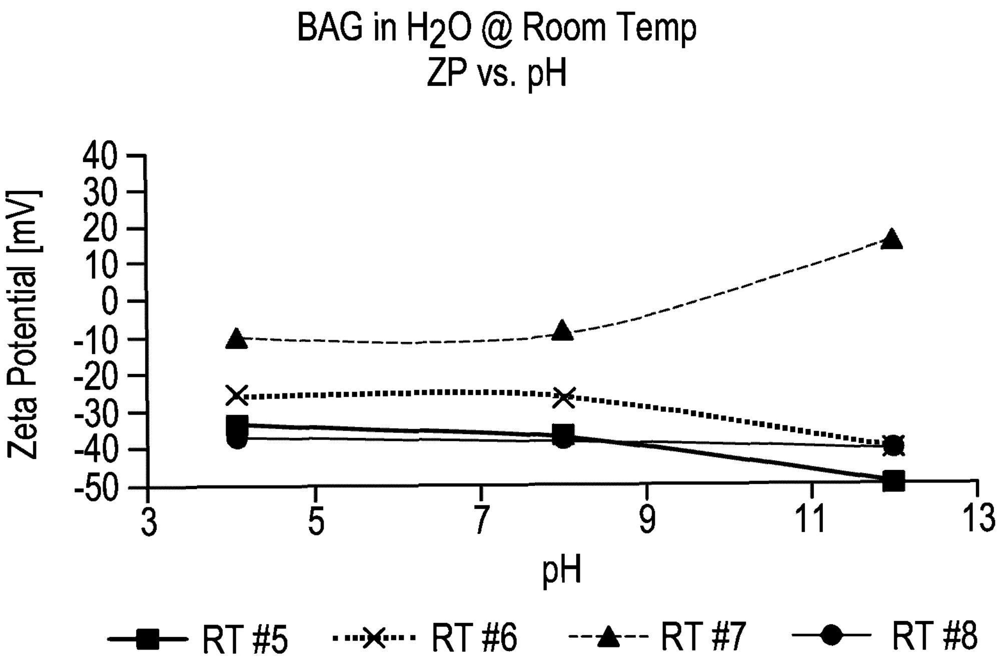
FIGS. 5A and 5B are graphs showing net surface charge characteristics of bioactive glass in aqueous solution across a pH range of 4 to 12 in accordance with one or more embodiments shown and described herein.
Figure 5B:
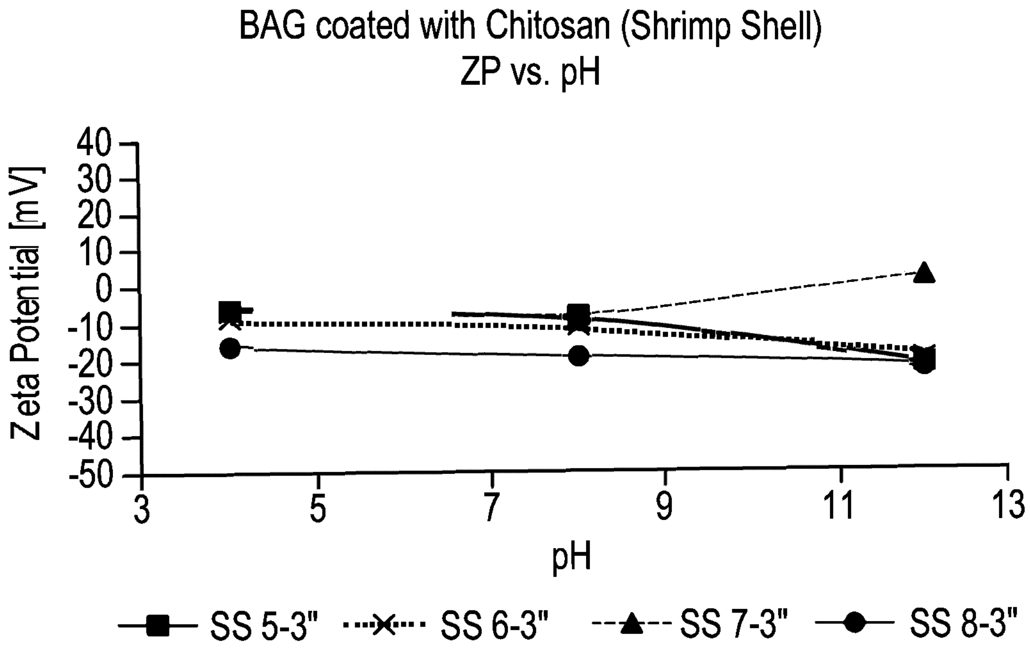

The surface charge measurement was examined by measuring the zeta potential (Malvern Zetasizer Nano ZS) at various pH values. The pH solutions were prepared using 0.01 M KCl adjusted to the pH level with dilute HCl or KOH. The samples were sonicated to mix then 35 μL of the sample was added to 950 mL of the pH solution and mixed. This was placed in a Malvern disposable folded capillary cell for testing. The RI value was 1.540. FIG. 5 illustrates surface charge by zeta potential of bioactive glass (unmodified in $H_2O$ (5A) and coated with chitosan (5B)) at pH 4, pH 8 and pH 12. In the figure, RT denotes pre-soaking in water at room temperature and SS denotes chitosan derived from shrimp shell. It is observed that for the unmodified BAG samples, the zeta potential increases with increase in pH for BAG #7, whereas it decreases for all other tested BAG samples. For the BAG samples which are modified with shrimp shell chitosan, similar trend is observed, however the change is not as pronounced as for the unmodified particles. This observation of surface charge by zeta potential could partially answer the nucleic acid binding-releasing mechanism from BAG surface. The exposed cations from bioactive glass particles also contribute the nucleic acid binding-releasing phenomenon, especially when the surface charge presents negative charge and the carrier composition is still able to capture negative charge of nucleic acid.

Example 3: DNA Modification of Bioactive Glass Composition

The BAG concentration aliquoted before surface modification is 20 mg/300 μL $H_2O$. The BAG concentration after surface modification is 10 mg/300 μL, and DNA concentration is 100 ng/10 μL for each of the preparation below.

DNA solution is added to each BAG solution and mixed well by vortexing, and then incubated at room temperature for 30 min in a microtube equipped with gentle shaker (300 rpm). The samples are centrifuged at 14,000 rpm for 5 min to obtain 10 μL supernatant sample for DNA quantification by Qubit HS dsDNA assay. If the Qubit Readout indicates that the BAG surface is not saturated by DNA, then 100 ng/10 μL DNA is add one more time and the solution is vortexed and incubated again for 30 min. This process of adding and quantification of the DNA is repeated several times for estimation of DNA payload.

Example 4: DNA Elution from Bioactive Glass Composition

The surface modified or unmodified BAG was centrifuged to remove all the supernatant for remaining DNA quantification. 300 μL of 50 mM pH5.4 phosphate buffer (170 mM ionic strength) was added to the BAG solution for elution. The solution is resuspended by vortex and incubated at room temperature for 30 min using a gentle shaker (300 rpm). The solution is centrifuged at 14,000 rpm for 5 min to remove all the supernatant for DNA quantification by Qubit HS dsDNA assay (10 μL sample for assay).

Figure 6:
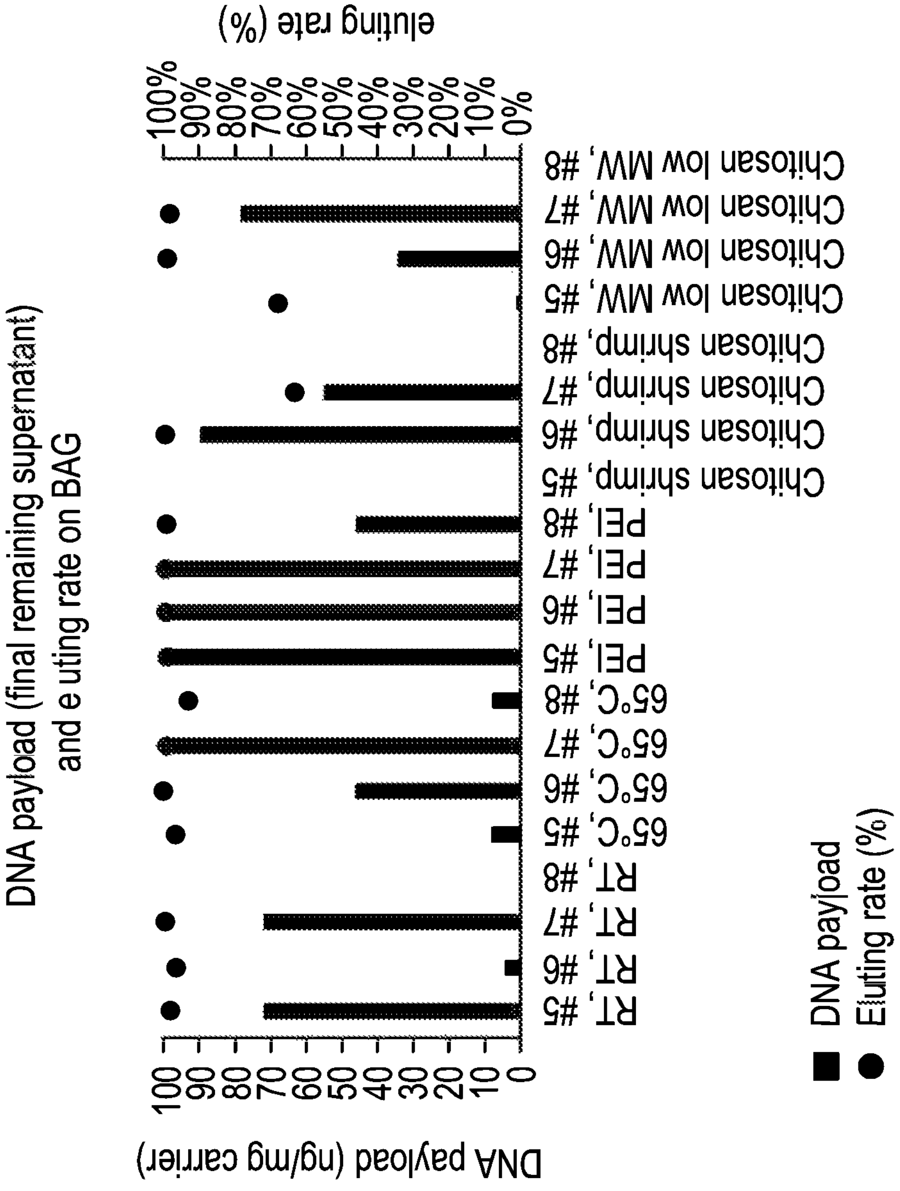
FIG. 6 is a graph showing DNA payload and elution rates for various bioactive glass compositions in accordance with one or more embodiments shown and described herein.
Figure 7A:
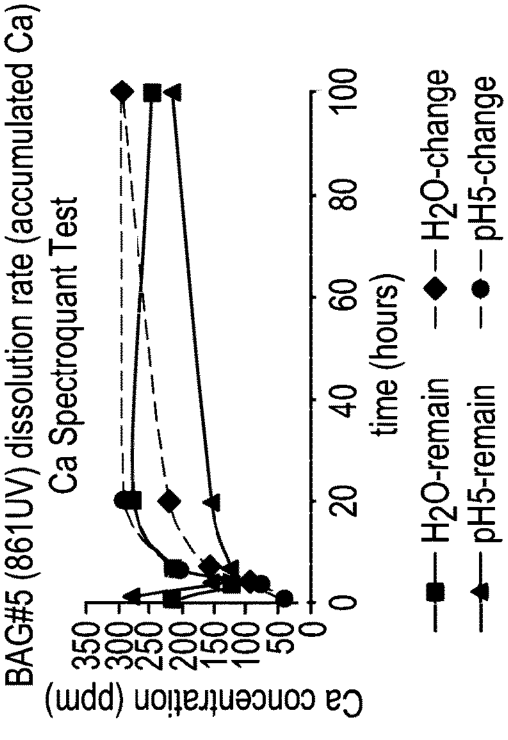
FIGS. 7A-7D are graphs showing dissolution kinetics by accumulated calcium concentration measured using modified Spectroquant® Calcium Cell Test for various bioactive glass compositions in accordance with one or more embodiments shown and described herein.
Figure 7B:
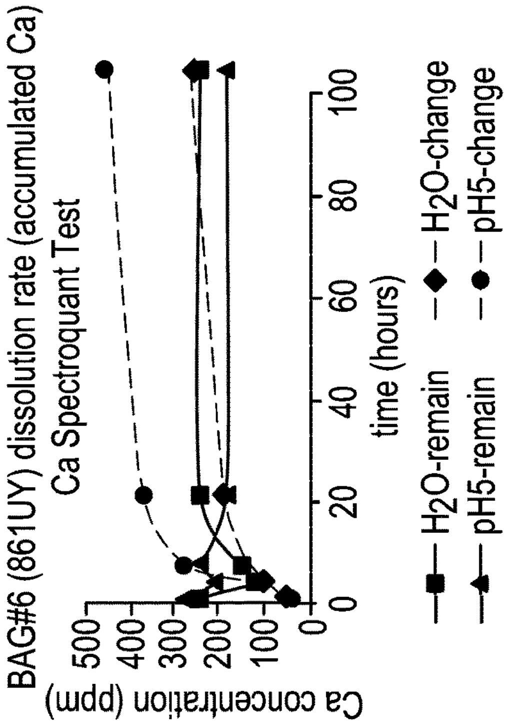
Figure 7C:
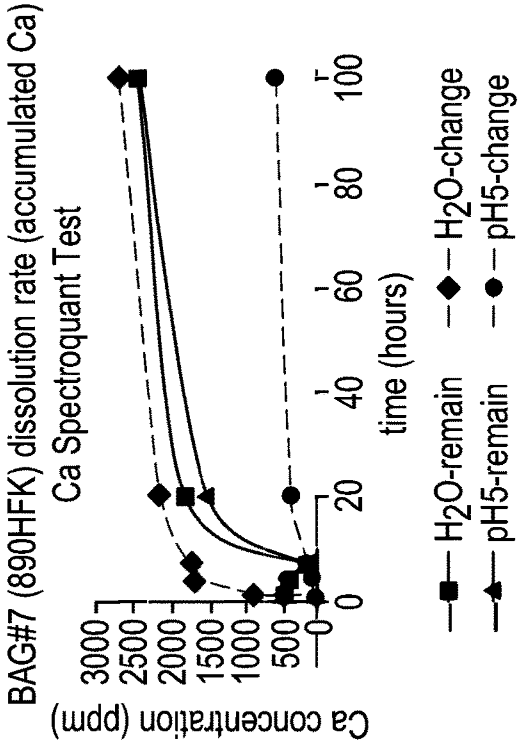
Figure 7D:
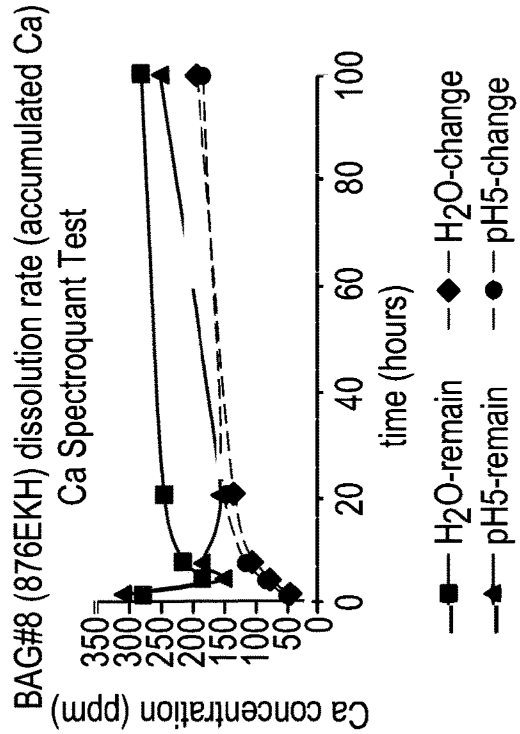

The results of DNA modification and DNA elution are as shown in FIG. 6, which demonstrates the potential of the BAG compositions, with or without surface modifier, for nucleic acid transfer and delivery into the target. Particularly, it was observed that the surface modifier can enhance the capacity of nucleic acid loading efficiency under neutral conditions and the captured DNA can be quantitatively released in the slightly acidic buffer system with 30 minutes or less eluting time.

Example 5: Solubility Test Process

Add 20 mg BAG (#5, #6 #7 and #8) and 0.2 mL water or 0.2 mL phosphate buffer into a 1.5 mL microtube and vortex mix. The mixtures are heated at 35° C. on a dry bath for time tracking. The solutions are vortex mixed prior to centrifugation. The mixtures are centrifuged down at 14000 rpm for 5 min. After centrifugation, the supernatant is removed from one group and replaced with fresh water or buffer after examination. For another group, 15 μL is sampled out for pH testing and refilled with 15 μL fresh water or buffer after examination.

Example 6: Calcium Cell Test

The calcium concentration was quantified by Merck Spectroquant® Calcium Cell Test at different time points with UV detection. 400 μL of buffer solution was aliquoted from the cell to 10 microtubes and 100 μL of Reagent Ca-1K and 100 μL of BAG samples was added to each microtube. pH value is about 7 for standard and samples. After waiting for 3 min, 50 μL of Reagent Ca-2K was added to each microtube. NanoDrop Microvolume Spectrophotometer (20 μL samples) was used to measure the change in calcium concentration within 1 hour. The results are as shown in FIG. 7, which demonstrates that the glass particles quickly release Ca ion in the first 24 hours, and then slowly but steady degraded along with the time.

Example 7: RNA modification of Bioactive Glass Composition

The process of Example 3 is repeated, except for replacing DNA with RNA. RNA is loaded on to unmodified as well as surface modified BAG particles and the results of RNA modification and RNA elution are studied.

All of the above examples will be performed using RNA instead of DNA.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth). Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed above. Finally, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

The drawings shall be interpreted as illustrating one or more embodiments that are drawn to scale and/or one or more embodiments that are not drawn to scale. This means the drawings may be interpreted, for example, as showing: (a) everything drawn to scale, (b) nothing drawn to scale, or (c) one or more features drawn to scale and one or more features not drawn to scale. Accordingly, the drawings can serve to provide support to recite the sizes, proportions, and/or other dimensions of any of the illustrated features either alone or relative to each other. Furthermore, all such sizes, proportions, and/or other dimensions are to be understood as being variable from 0-100% in either direction and thus provide support for claims that recite such values or any and all ranges or subranges that may be formed by such values.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "technology," etc., are not meant to invoke exception (b) or otherwise restrict the scope of the recited claim terms. Other than situations where exception (b) applies, nothing contained in this document should be considered a disclaimer or disavowal of claim scope.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

In addition, where features or aspects of the disclosure are described in terms of Markush groups, those skilled in the art will recognize that the disclosure is also thereby described in terms of any individual member or subgroup of members of the Markush group.

Unless the context indicates otherwise, it is specifically intended that the various features of the technology described herein may be used in any combination. Moreover, the disclosure also contemplates that in some embodiments, any feature or combination of features set forth herein may be excluded or omitted. To illustrate, if the specification states that a complex comprises components A, B and C, it is specifically intended that any of A, B or C, or a combination thereof, may be omitted and disclaimed singularly or in any combination.

Unless explicitly indicated otherwise, all specified embodiments, features, and terms intend to include both the recited embodiment, feature, or term and biological equivalents thereof.

All patents, patent applications, provisional applications, and publications referred to or cited herein are incorporated by reference in their entirety, including all figures and tables, to the extent they are not inconsistent with the explicit teachings of this specification.

What is claimed is:

1. A pH-switchable carrier composition comprising:

a plurality of bioactive glass particles, wherein each of the bioactive glass particles is optionally at least partially coated with a surface modifier;

wherein the plurality of bioactive glass particles comprise a nucleic acid compound non-covalently bound to a surface of the bioactive glass particles; and wherein the bioactive glass particles, with or without the surface modifier, are configured to bind to the nucleic acid compound upon contact at pH in the range of 7 to 11, and exhibit controlled release of the nucleic acid compound at pH in the range of 5 to 6.

2. The pH-switchable carrier composition of claim 1, wherein the bioactive glass particle mainly comprises, expressed in terms of weight percent on the oxide basis, from about 30% to about 75% $SiO_2$, from about 2% to about 40% CaO and from about 3% to about 15% $P_2O_5$.

3. The pH-switchable carrier composition of claim 2, wherein the bioactive glass particle further comprises, expressed in terms of weight percent on the oxide basis:

from about 0% to about 5% $B_2O_3$;

from about 0% to about 5% $Al_2O_3$;

from about 0% to about 20% MgO;

from about 0% to about 10% $ZrO_2$;

from about 0% to about 5% F; and from about 0% to about 30% $R_2O$, wherein $R_2O$ comprises from about 0% to about 10% $K_2O$ and from about 0% to about 30% $Na_2O$.

4. The pH-switchable carrier composition of claim 1, wherein the bioactive glass particle mainly comprises, expressed in terms of weight percent on the oxide basis, from about 30% to about 70% $B_2O_3$, from about 5% to about 25% CaO and from about 1% to about 10% $P_2O_5$.

5. The pH-switchable carrier composition of claim 4, wherein the bioactive glass particle further comprises, expressed in terms of weight percent on the oxide basis:

from about 0% to about 5% $SiO_2$;

from about 0% to about 15% $Al_2O_3$;

from about 0% to about 10% MgO;

from about 0% to about 10% $ZrO_2$;

from about 0% to about 5% F; and from about 0% to about 20% $R_2O$, wherein $R_2O$ comprises from about 0% to about 20% $K_2O$ and from about 0% to about 10% $Na_2O$.

6. The pH-switchable carrier composition of claim 1, wherein the bioactive glass particle comprises a calcium phosphate glass.

7. The pH-switchable carrier composition of claim 1, wherein the bioactive glass particle is at least a partially coated with a surface modifier and the surface modifier comprises a polycationic compound.

8. The pH-switchable carrier composition of claim 7, wherein the polycationic compound is selected from the group consisting of polyamines, polylysine, polyarginine, polyornithine, polyalkylenimine, chitosan, poly alkyl aminoalkyl methacrylate and derivatives thereof, or any combination thereof.

9. The pH-switchable carrier composition of claim 8, wherein the polycationic compound is selected from the group consisting of polyethyleneimine, shrimp chitosan, low molecular weight chitosan and derivatives thereof.

10. The pH-switchable carrier composition of claim 9, wherein the molecular weight of low molecular weight chitosan or a derivative is from about 50 kDa to about 375 kDa.

11. The pH-switchable carrier composition of claim 1, wherein the nucleic acid compound is selected from the group consisting of a ribonucleic acid compound, a deoxyribonucleic acid compound, and derivatives thereof.

12. The pH-switchable carrier composition of claim 1, wherein the bioactive glass particles have a particle size of about 1 μm to about 10 μm.

13. The pH-switchable carrier composition of claim 12, wherein the bioactive glass particles have a particle size of about 1 μm to about 5 μm.

14. The pH-switchable carrier composition of claim 1, wherein a zeta-potential of the unmodified bioactive glass particles is from about −10 mV to about −40 mV under neutral conditions.

15. The pH-switchable carrier composition of claim 1, wherein a zeta-potential of the surface modified bioactive glass particles is from about 0 mV to about −20 mV under neutral conditions.

16. The pH-switchable carrier composition of claim 1, wherein the concentration of the nucleic acid ranges from about 5 ng/mg to about 10 μg/mg of the total weight of the carrier composition.

17. A plurality of bioactive glass particles, comprising:

optionally a surface modifier at least partially coating the plurality of bioactive glass particles;

a nucleic acid compound non-covalently bound to a surface of the bioactive glass particles; and wherein the bioactive glass particles, with or without the surface modifier, are configured to bind to the nucleic acid compound upon contact at pH in the range of 7 to 11, and exhibit controlled release of the nucleic acid compound at pH in the range of 5 to 6; and wherein the bioactive glass particle mainly comprises, expressed in terms of weight percent on the oxide basis:

(a) from about 30% to about 75% $SiO_2$, from about 2% to about 40% CaO and from about 3% to about 15% $P_2O_5$; or (b) from about 30% to about 70% $B_2O_3$, from about 5% to about 25% CaO and from about 1% to about 10% $P_2O_5$.

18. A vehicle comprising the pH-switchable carrier composition according to claim 1.

19. The vehicle of claim 18, wherein the vehicle comprises a drug delivery vehicle, a gene delivery vehicle, a tissue regeneration vehicle, a crop treatment or crop protection, an immunomodulatory vehicle, or a gene editing complex vehicle.

20. A method of manufacturing a pH-switchable carrier composition, the method comprising:

processing a bioactive glass into fine particles;

mixing the fine particles of bioactive glass with a liquid medium to form a solution;

optionally modifying the surface of the bioactive glass particles in the solution with a surface modifier to form surface-modified bioactive glass particles, contacting the bioactive glass particles or the surface-modified bioactive glass particles with a nucleic acid compound in a liquid medium to form an admixture; and incubating the admixture under conditions in which the nucleic acid compound non-covalently binds to the bioactive glass particles or the surface-modified bioactive glass particles, wherein the bioactive glass particles, with or without the surface modifier, are configured to bind to the nucleic acid compound upon contact at pH in the range of 7 to 11, and exhibit controlled release of the nucleic acid compound at pH in the range of 5 to 6.

21. The method of claim 20 comprising modifying the surface of the bioactive glass particles by incubating the bioactive glass particles with a surface modifier to form the surface-modified bioactive glass particles.

22. The method of claim 21, wherein the surface modifier comprises a polycationic compound.

23. The method of claim 21, wherein incubation of the bioactive glass particles with a surface modifier is conducted at a temperature of about ambient temperature to about 65° C.

24. The method of claim 21, wherein incubation of the bioactive glass particles with a surface modifier is conducted for a period of about 8 to 24 hours.

25. The method of claim 21, further comprising:

contacting the surface-modified bioactive glass particles with a nucleic acid compound in a liquid medium to form an admixture; and incubating the admixture under conditions in which the nucleic acid compound non-covalently binds to the surface-modified bioactive glass particles.

26. The method of claim 25, wherein the incubation of surface-modified bioactive glass particles with the nucleic acid is conducted at room temperature.

27. The method of claim 25, wherein the incubation of surface-modified bioactive glass particles with the nucleic acid is conducted for a period of about 15 min to 2 hours.

28. The method of claim 20, wherein the liquid medium is selected from the group consisting of water, alcohols or hydrocarbons.

29. The method of claim 20, wherein the bioactive glass particle mainly comprises, expressed in terms of weight percent on the oxide basis, from about 30% to about 75% $SiO_2$, from about 2% to about 40% CaO and from about 3% to about 15% $P_2O_5$.

30. The method of claim 29, wherein the bioactive glass particle further comprises, expressed in terms of weight percent on the oxide basis:

from about 0% to about 5% $B_2O_3$;

from about 0% to about 5% $Al_2O_3$;

from about 0% to about 20% MgO;

from about 0% to about 10% $ZrO_2$;

from about 0% to about 5% F; and from about 0% to about 30% $R_2O$, wherein $R_2O$ comprises from about 0% to about 10% $K_2O$ and from about 0% to about 30% $Na_2O$.

31. The method of claim 20, wherein the bioactive glass particle mainly comprises, expressed in terms of weight percent on the oxide basis, from about 30% to about 70% $B_2O_3$, from about 5% to about 25% CaO and from about 1% to about 10% $P_2O_5$.

32. The method of claim 31, wherein the bioactive glass particle further comprises, expressed in terms of weight percent on the oxide basis:

from about 0% to about 5% $SiO_2$;

from about 0% to about 15% $Al_2O_3$;

from about 0% to about 10% MgO;

from about 0% to about 10% $ZrO_2$;

from about 0% to about 5% F; and from about 0% to about 20% $R_2O$, wherein $R_2O$ comprises from about 0% to about 20% $K_2O$ and from about 0% to about 10% $Na_2O$.

* * * * *